United States Patent [19]
Pollock et al.

[11] Patent Number: 5,434,078
[45] Date of Patent: Jul. 18, 1995

[54] FERMENTATION BROTH COMPRISING XANTHAN GUM FROM DAIRY PERMEATES AND OTHER FILTERED DAIRY PRODUCTS

[75] Inventors: Thomas J. Pollock, San Diego; Richard W. Armentrout, La Jolla, both of Calif.

[73] Assignees: Shin-Etsu Bio, Inc., San Diego, Calif.; Shin-Etsu Chemical Co., Ltd., Tokyo, Japan

[21] Appl. No.: 60,403

[22] Filed: May 11, 1993

Related U.S. Application Data

[63] Continuation-in-part of Ser. No. 517,551, Apr. 24, 1990, Pat. No. 5,279,961, which is a continuation of Ser. No. 180,945, Apr. 12, 1988, abandoned, which is a continuation-in-part of Ser. No. 38,302, Apr. 14, 1987, abandoned.

[51] Int. Cl.$^6$ .................... C12P 19/06; C12N 1/20; C08B 9/00
[52] U.S. Cl. .................. 435/253.6; 435/101; 435/104; 536/114
[58] Field of Search ............ 536/114; 435/101, 252.3, 435/104, 253.6

[56] References Cited

PUBLICATIONS

Thorne et al. (1988) J. Ind. Microb. 3: 321–328.

*Primary Examiner*—Richard A. Schwartz
*Assistant Examiner*—Philip W. Carter
*Attorney, Agent, or Firm*—McAulay Fisher Nissen Goldberg & Kiel

[57] ABSTRACT

The present invention relates to the unexpected discovery that xanthan gum can be produced from filtered whey or milk products, including whey permeates and milk permeates, by a fermentation process which uses organisms which are capable of converting lactose to xanthan gum.

4 Claims, 1 Drawing Sheet

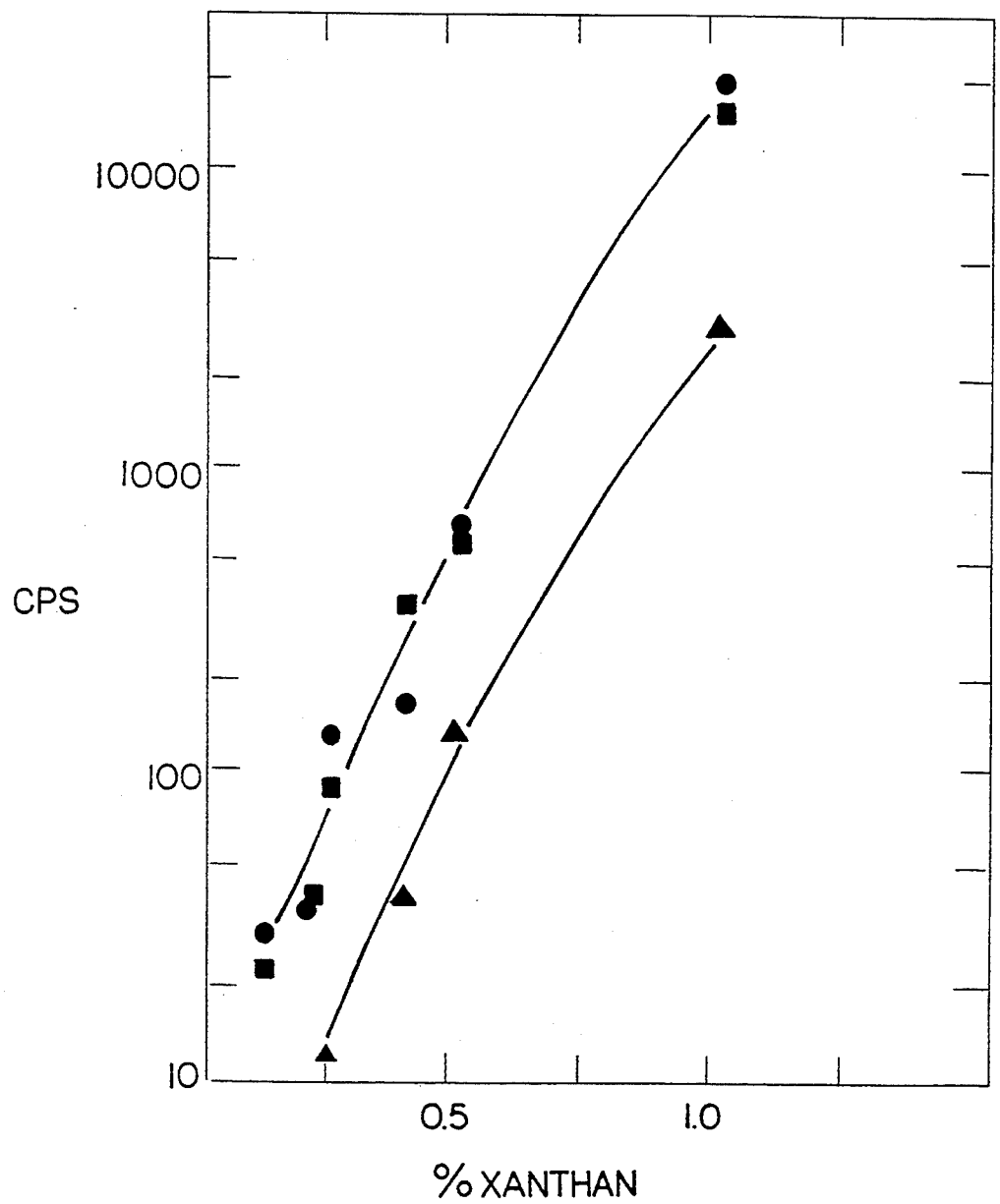

FERMENTATION BROTH COMPRISING XANTHAN GUM FROM DAIRY PERMEATES AND OTHER FILTERED DAIRY PRODUCTS

CROSS-REFERENCE TO RELATED APPLICATIONS

This application is a continuation-in-part of application Ser. No. 07/517,551, filed Apr. 24, 1990, now U.S. Pat. No. 5,279,961, which, in turn, is a continuation of application Ser. No. 07/180,945, filed Apr. 12, 1988, now abandoned, which is a continuation-in-part of application Ser. No. 07/038,302, filed Apr. 14, 1987, now abandoned, the contents of all of which are hereby incorporated by reference.

BACKGROUND OF THE INVENTION

Xanthan gum is a commercially important viscosifier produced by the fermentation of glucose, starch, or sucrose by strains of the bacteria *Xanthomonas campestris*. Production costs for xanthan gum are comparatively high and commercial applications could be greatly expanded if costs were reduced. A significant fraction of the production cost of xanthan gum is attributed to the raw material carbohydrate substrates. Therefore, it is desirable to develop methods to produce xanthan gum which use low-cost sugars or other substrates.

In our prior applications, Ser. Nos. 07/517,551 and 07/180,945, we have described an engineered strain of *Xanthomonas campestris* which is able to utilize lactose as a substrate and provide a high productivity of high quality xanthan gum product. As shown therein, this strain effectively utilizes relatively pure lactose, or whey as a substrate.

In the dairy industry, efforts are made to recover as much of the usable protein and other organic values as possible. For this purpose, the whey or milk is filtered and the recovered solids, which include the predominant portion of the protein and other non-lactose values, are used for commercial purposes and products. The remainder, i.e., the filtrate or permeate as it is sometimes called, is usually considered to be a waste. Processes have been developed to remove some of the lactose from the permeate. The resulting waste stream from the processing of permeate, known as "Low Lactose Permeate", or "LLP", has less value than does the unfractionated permeate.

A problem that has been encountered in the use of whey for the production of xanthan gum using presently available commercial processes, is that the xanthan product obtained is of poor quality, i.e., low viscosity.

SUMMARY OF THE INVENTION

We have discovered that excellent yields of high quality xanthan gum can be produced from filtered dairy fluids, including whey LLP and milk permeates, by a fermentation process which uses organisms which are capable of converting lactose to xanthan gum. The xanthan gum obtained exhibits superior viscosity characteristics compared to that produced from unfiltered whey.

In particular, we have found that by first subjecting milk or whey to filtration as defined herein and then subjecting a lactose utilizing strain of *Xanthamonas campestris* to fermentation conditions utilizing the filtrate as the substrate, high quality xanthan gum can be obtained in good yield.

Accordingly, the present invention has at least the following objects:

a) to provide a method for making xanthan gum from filtered dairy fluids, including whey permeates or milk permeates;

b) to provide a method for the production of high viscosity xanthan gum from filtered dairy fluids, including whey permeates or milk permeates;

c) to provide a fermentation broth which may be used to produce a high quality xanthan gum from filtered dairy fluids, including whey permeates or milk permeates;

d) to provide a fermentation broth from which the recovery of a high quality xanthan gum is commercially feasible; and e) to provide a high quality xanthan gum using filtered diary fluids.

These and other objects of the present invention may be readily gleaned from the detailed description of the invention which follows.

DESCRIPTION OF THE DRAWING

The drawing shows the variation in viscosity with concentration of xanthan gum made by the fermentation of glucose, lactose, or whey.

In the drawing, the symbols have the following meanings:
circle=X59 fermenting glucose
square=X59-1232 fermenting lactose
triangle=X59-1232 fermenting whey.

DETAILED DESCRIPTION OF THE INVENTION

The following definitions will be used throughout the specification in describing the instant invention.

The term "dairy fluid" is used collectively to designate milk or fluid products obtained from the processing of milk and includes whey.

The term "whey" is used throughout the specification to describe the liquid recovered following the curdling or precipitation of solids from milk or dairy fluid during the manufacture of cheese, cheese substitute or related curdled and/or precipitated dairy products. The term whey also includes dried forms of the liquid whey.

The terms "permeate" or "filtrate" are used interchangeably throughout the specification and mean the fluid recovered after the treatment of whey, milk or other dairy fluid by filtration (generally, ultrafiltration) which separates components of the fluid by molecular size and generally removes proteins, such as, lactalbumin. It is understood that the permeate liquid may contain solids, albeit of relatively small molecular weight or size so as to pass through the filter. Permeate also refers to dried forms of the liquid. More particularly, a permeate may be the milk, milk product or whey material that passes through a semi-permeable filtration membrane, where the membrane or filter is selected to substantially retain protein and pass lactose. Typical permeates of whey, milk or other dairy fluids contain relatively high concentrations of lactose, and small amounts of protein (generally less than about 5% by dry weight of the permeate), and as well as minor amounts of other constituents.

In general, permeate contains no more than about 5% by weight protein (based upon the dry weight of the permeate), and most preferably no more than about 3% by weight protein (dry weight), the protein having a molecular weight generally no greater than about 20,000 dalton units, although minor amounts of protein having a molecular weight of about 50,000 dalton units or more. Preferably, the permeate contains as little protein as possible, most preferably less than about 2% of the dry weight of the permeate. Normally, permeate contains at least about 50% by weight lactose (based upon the dry weight of the permeate) as well as minerals, vitamins, organic acids, fat and other minor constituents.

The term "low lactose permeate or LLP" is used throughout the specification to describe permeate which has been treated to remove some of the lactose. The term LLP includes the dried forms of this permeate. Lactose is removed from permeate generally by a precipitation process in which the lactose is selectively precipitated from permeate.

The term "viscosity" is used throughout the specification, unless otherwise indicated, to signify a 0.25% w/v aqueous solution of xanthan gum determined at room temperature using a No. 18 spindle of a Brookfield digital viscometer at a shear rate of 1 $s^{-1}$.

Mutant and engineered microorganisms of the genus Xanthomonas including for example, strains of Xanthomonas sp., have been produced which are capable of converting the lactose in whey to xanthan gum. Microorganisms, including bacterial strains which are capable of being used in the present invention, include, for example, any microorganism having a modification (spontaneous, induced or genetically engineered) which exhibits an increase in the production of xanthan gum from lactose. Within this broad category of useful microorganisms are numerous species of Xanthomonas, including *X. campestris, X. albilineans, X. axonopodis, X. fragariae, X. gummosudans, X. juglandis, X. mannihotis, X. phaseoli, X. vasculorum,* among others. Certain *Xanthomonas campestris* strains, such as, engineered *Xanthomonas campestris*, for example, X59-1232 (ATCC 55258), are preferred for their ability to increase xanthan production from lactose. Specific genetic modifications capable of increasing xanthan production in *Xanthomonas campestris* on lactose include mutations or the introduction of exogenous genetic information controlling the synthesis of xanthan from lactose introduced into *Xanthomonas campestris* strains.

The present invention relates to an unexpected result fortuitously discovered in the fermentation of lactose to xanthan gum by microorganisms. It has been discovered that the fermentation of milk, dairy fluids or whey substrate which has been filtered to remove proteins and other chemical components having molecular weights above about 20,000 dalton units and to pass lactose in the presence of a microorganism capable of convening lactose to xanthan gum in a fermentation medium produces an unexpectedly higher quality xanthan gum having a substantially greater viscosity than xanthan gum produced under the same conditions from the unfiltered precursor of the substrate. Unfiltered precursor of the substrate refers to the material which is filtered to produce the substrate.

For purposes of presenting experimental evidence related to the discovery of this invention, we have selected one of the strains of *Xanthomonas campestris* strains (X59-1232, ATCC 55258) because the parent strain, X59 (ATCC 55298), was also available for direct comparison (each of these strains has been described in the parent applications referred to above).

The previously described invention will be better understood by the following examples which are provided to illustrate the present invention and should not be misunderstood or misinterpreted to limit the scope of the present invention in any way.

EXAMPLES

Whey (Sigma) and milk permeate (Land O'Lakes) were obtained from commercial suppliers and used as the source of lactose in the fermentation media for the production of xanthan gum. The fermentation media contained between 0.5 to 6% (w/v) lactose, usually about 1% to about 5%. The media was inoculated with the *Xanthomonas campestris* in the usual manner and fermentation was carried out at between 20° to 35° C. for 1 to 10 days using apparatus and techniques well known to the industry. The xanthan gum can then be recovered from the broth by any of a number of well established techniques readily recognized by one of ordinary skill in the art, including precipitation, ultrafiltration, drying, spray drying and the like.

EXAMPLE 1

Quality of X.gum produced from whey

The following cultures were grown in shake flasks containing 200 ml of the medium having the composition set forth in Table 1, supplemented with the indicated carbohydrate at 2% (w/v): X59, glucose; X59-1232, lactose; X59-1232, whey. After 48 h growth the culture contents were precipitated with 2 volumes of isopropyl alcohol, dried and ground. Samples were resuspended at specific weight percentages with the weights determined to the exclusion of water, protein and ash. For viscosity measurements, the dried precipitate was ground in a mortar and sieved through a 250 micron mesh before resuspending in 0.1% (w/v) NaCl. Viscosity measurements over a range of shear rates at room temperature were made with a Brookfield LVT viscometer (see the Figure).

TABLE 1

| Medium | Inorganic Minerals | Nitrogen Source (g/l) |
|---|---|---|
| | (g/l) | |
| K$_2$HPO$_4$ | 3.5 | 10 Difco peptone |
| KH$_2$PO$_4$ | 2.6 | |
| MgSO$_4$.7H$_2$O | 0.26 | |
| | (mg/l) | |
| H$_3$BO$_3$ | 6 | |
| ZnO | 6 | |
| FeCl$_3$.6H$_2$O | 2.6 | |
| CaCO$_3$ | 20 | |

Whey from Sigma is typical of whey generally available and contains 65% lactose, 13% protein, 8% ash, and 2% lactic acid by dry weight. Prior to fermentation, a 30% (w/v) solution of whey was autoclaved at 121° C. for 20 min and centrifuged.

The drawing shows the viscosity of xanthan gum made by fermentation of glucose, lactose, or whey according to this example. Solutions of xanthan gum were prepared at the defined concentrations (excluding the weight of water, protein and ash). Viscosities at different shear rates were measured and the values from a shear rate of 1.32 $s^{-1}$ (1 rpm) for spindle number 18, (Brookfield) were plotted as set forth in FIG. 1 using the following symbols, strains, and growth or processing conditions:

Circle, X59 fermenting glucose.
Square, X59-1232 fermenting lactose.
Triangle, X59-1232 fermenting whey.

The solution viscosities for the xanthan gum made by X59 from glucose or X59-1232 from lactose were not distinguishable. However, the material made by X59-1232 from whey was less viscous, requiring almost twice as much by weight to give equal viscosity. This example demonstrates that the xanthan gum made from whey is of lower viscosity than that made from either glucose or lactose.

EXAMPLE 2

Viscosity of Xanthan Produced from Milk Permeate

This example compares the viscosity of xanthan gum produced by X59-1232 on milk permeate with that produced by X59 on glucose. Viscosity of a 0.25% solution ($\mu$, viscosity at a shear rate of 1 per sec) is approximately the same for gum produced on glucose or milk permeate.

The X59 gum was produced in a batch fermentor at the 3 L scale with a medium consisting of glucose (2% w/v), $NH_4NO_3$ and the inorganic minerals listed in Example 1. The fermentor was a Bioflow III (New Brunswick), 5 L capacity. pH was controlled by base additions.

The X59-1232 samples were prepared from shake flask fermentations. The flasks (250 ml capacity) contained 50 ml of medium consisting of 2.3% (w/v) milk permeate, and either $NH_4Cl$ or $NH_4NO_3$, and the inorganic minerals listed in Example 1. After 48 h, samples were precipitated using IPA. Dried xanthan gum samples were each re-hydrated to a uniform 0.25 % (w/v) solution in deionized water. The viscosity of about 10 ml of each solution was determined at room temperature using the No. 18 spindle on a Brookfield digital viscometer at a range of rpm's. The viscosity ($\mu$) at a shear rate of 1 per sec was calculated, using a linear regression program, from the relationship: the Log of centipoise versus log of shear rate. The results are set forth in Table 2.

TABLE 2

| SAMPLE | $\mu$ |
| --- | --- |
| X59/GLUCOSE | |
| $NH_4NO_3$ medium | 240 |
| X59-1232/MILK PERMEATE | |
| $NH_4Cl$ medium | 235 |
| $NH_4NO_3$ medium | 282 |

What is claimed is:

1. A fermentation broth resulting from the submerged fermentation of *Xanthomonas campestris* in the presence of inorganic minerals, a nitrogen source, and a whey or dairy fluid filtered to pass lactose and remove proteins having a size of at least about 20,000 dalton units comprising xanthan gum produced from the fermentation, inorganic minerals, a nitrogen source, and a whey or dairy fluid filtered to pass lactose and remove proteins having a size of at least about 20,000 dalton units.

2. The fermentation broth according to claim 1 in a dried form.

3. The fermentation broth according to claim 1 wherein said dairy fluid is low lactose permeate.

4. The fermentation broth according to claim 1 wherein said dairy fluid is milk permeate or whey permeate.

* * * * *